United States Patent [19]
Rocha

[11] Patent Number: 5,925,250
[45] Date of Patent: Jul. 20, 1999

[54] CONCENTRATOR & FILTER HAVING PROTECTED END PORTION

[75] Inventor: Andrew John Rocha, Long Beach, Calif.

[73] Assignee: Medical Chemical Corp., Torrance, Calif.

[21] Appl. No.: 09/001,038

[22] Filed: Dec. 30, 1997

[51] Int. Cl.⁶ .................................................. B01D 35/28
[52] U.S. Cl. ......................... 210/436; 210/446; 210/453; 210/455; 210/472; 210/474; 209/172; 209/173; 422/99; 422/100; 422/101
[58] Field of Search .................... 210/436, 446, 210/453, 455, 464, 472, 474; 209/3, 17; 422/99, 101, 102; 435/284, 286

[56] References Cited

U.S. PATENT DOCUMENTS

| | | | |
|---|---|---|---|
| D. 382,963 | 8/1997 | Didier | D24/162 |
| 4,783,318 | 11/1988 | Lapakko | 422/101 |
| 5,104,533 | 4/1992 | Szabados | 210/257.1 |
| 5,482,618 | 1/1996 | Hall | 210/85 |
| 5,489,385 | 2/1996 | Raabe et al. | 210/448 |
| 5,501,841 | 3/1996 | Lee et al. | 422/101 |
| 5,518,612 | 5/1996 | Kayal et al. | 210/232 |
| 5,534,228 | 7/1996 | Wesseler | 422/103 |
| 5,556,544 | 9/1996 | Didier | 210/436 |
| 5,601,711 | 2/1997 | Sklar et al. | 210/238 |
| 5,603,900 | 2/1997 | Clark et al. | 422/101 |
| 5,624,554 | 4/1997 | Faulkner et al. | 210/232 |

*Primary Examiner*—David A. Reifsnyder
*Attorney, Agent, or Firm*—Cislo & Thomas LLP

[57] ABSTRACT

A fecal parasite concentrator which has a cylindrical body (20) with connections for a sample vial (24) on one end having a protective recess (27) for receiving the sample vial and a centrifuge tube (28) on the other. An integral filter (36) is disposed within the body at right angles coaxially covering the cross sectional area of the hollow body. The filter contains a series of closely spaced square openings for filtration of a liquid diluted fecal specimen. A hollow stem (40) with truncated end (44) extends upwardly from the filter having orifices (46) which permit air to pass therethrough when the diluent specimen flows through the filter.

10 Claims, 2 Drawing Sheets

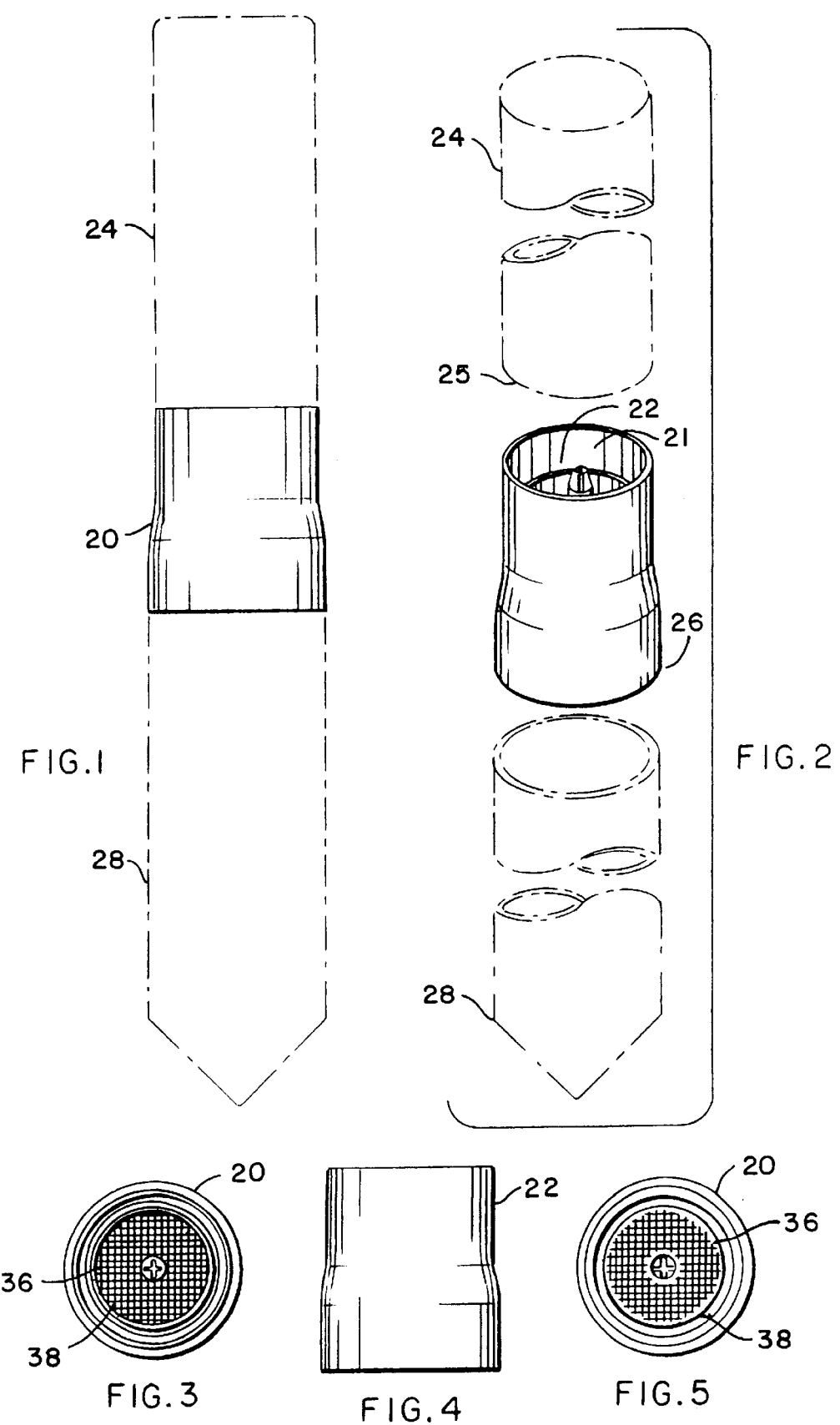

CONCENTRATOR & FILTER HAVING PROTECTED END PORTION

BACKGROUND OF THE INVENTION

1. Field of the Invention

This invention relates to filters for processing fecal samples to separate parasite eggs and larvae. More specifically, the invention pertains to a filter having connections for a sample vial and a centrifuge tube including a hollow stem for equalizing pressure therebetween, wherein there is an upstanding skirt portion to act as a protector for the one end of the filter when associated with the sample vial. This invention is an improvement to the concentrator and filter described and claimed in issued U.S. Patent No. 5,556,544.

2. Background Art

Previously, many types of filters have been used in endeavoring to provide an effective means for the separation of parasite eggs and larvae from feces samples. Over the years, many types of devices have been developed to concentrate parasitic eggs and larvae also protozoan cysts and to recover coccidian occysts such as isopora belli and crytosporidium parvium.

A search of the prior art did not disclose any patents that read directly on the claims of the instant invention, however, the following U.S. patents are considered related:

| U.S. Patent No. | Inventor | Issued |
| --- | --- | --- |
| 5,556,544 | Didier | September 17, 1996 |
| 4,081,356 | Zierdt | March 23, 1978 |
| 4,675,110 | Fay | June 23, 1987 |

As indicated, the invention herein is an improvement over the concentrator and filter of U.S. Pat. No. 5,556,544 in that an upstanding skirt portion extends upwardly to over an end portion of the sample unit so as to prevent contamination, as with fecal matter.

U.S. Pat. No. 4,081,356 to Zierdt discloses a current device and method for recovering parasitic eggs and larvae from feces samples. In this device, a cup is attached to an open ended tube forming an emulsification chamber. A filter is attached to the chamber which includes a coaxial tube for the passage of air and a centrifuge tube is attached by an annular collar to form a separating chamber.

U.S. Pat. No. 4,675,110 to Fay discloses a device and method for the concentration of parasite eggs and larvae. The device consists of separable upper and lower chambers connected by a mid-piece which incorporates a filter of stainless steel gauze.

Other systems and methods have been utilized for the same purposes such as the fecal parasite, concentrator known by its registered trademark FPC and JUMBO and manufactured by Evergreen Scientific of Los Angeles, Calif. The JUMBO concentrator functions in the same manner as described above and connects a vial and tube together as with Fay's teachings. A movable vent-straw is located in the center of the strainer unit and requires manually pulling the straw out approximately 1.0 inch (2.54 cm) prior to attachment of the specimen vial. The problems of clogging and blocking the pressure equalizing element still exist and multiple components are employed.

For background purposes and as indicative of the art to which the invention relates reference may be made to the remaining cited patents.

| U.S. Patent No. | Inventor | Issued |
| --- | --- | --- |
| 4,783,318 | Lapakko | November 8, 1988 |
| 5,104,533 | Szabados | April 14, 1992 |
| 5,489,385 | Raabe, et al. | February 6, 1996 |
| 5,482,618 | Hall | January 9, 1996 |
| 5,501,841 | Lee, et al. | March 26, 1996 |
| 5,518,612 | Kayal, et al. | May 21, 1996 |
| 5,534,228 | Wesseler | July 9, 1996 |
| 5,624,554 | Faulkner, et al. | April 29, 1997 |
| 5,601,711 | Sklar, et al. | February 11, 1997 |
| 5,603,900 | Clark et al. | February 18, 1997 |

DISCLOSURE OF THE INVENTION

While much effort has been applied in the field for this specific method of separating fecal test samples, there is still room for improvement. The simplicity of using standard well known and readably available vials and tubes has been accepted by prior art in general. However, when utilizing a concentrator and filter such as that disclosed in Didier U.S. Pat. No. 5,556,544, filling the vial or tube with the sample to be tested may cause contaminants to adhere to the threads or the like and possibly contaminate or cross contaminate the test site. That is, when the vial or tube, which has a threaded end and which contains the original sample to be tested is inverted, once associated with the filter and concentrator, fecal matter on the outside rim or threads of the tube or vial may cause contamination, by reason thereof, of the test site.

With the upstanding or upwardly directed skirt or sheath surrounding the exterior mating portion of the tube or vial, the possibility of contamination and cross contamination is greatly reduced.

It is therefore a primary object of the invention to provide an equalizing device that resists clogging and blocking while permitting air to pass through the device with a decrease in the risk of contamination. Thus, allowing the vapor pressure to balance on each side of the filter screen quickly with a minimum amount of required agitation. This object is achieved using a hollow stem in the center of the filter that has a tapered inside diameter and that extends partially into the sample vial. An upstanding, circumferential portion acts as a catch for any contaminant on the exterior of the collection tube or vial.

An important object of the invention is the simplicity of manufacture, as the entire device including the skirt, connecting means, filter and hollow stem are formed of a single, integral molded part. Hermetic seals are easily achieved with the vial and tube and no other parts are necessary to handle or manipulate.

Another object of the invention is directed to the minimal cost of the device as it is fabricated by an injection molded process. This process requires only an initial cost for the tooling after which, multiple units may then be rapidly and inexpensively produced.

Still another object of the invention is its ease of understanding and use. Since only one single part is required to be used in combination with well known vials and tubes, the actual mechanics are easily understood and used by any knowledgeable technician.

A further object of the invention is the positive seal created by an interference fit for the vial and a threaded joint for the tube wherein a surrounding, upstanding portion provides a catch-all for any contaminant adhering to the threaded end of the tube or vial. Both of these sealing methods create a positive hermetic closure which eliminates leakage that would invalidate the sample and reduces the risk of contamination.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 1 is an elevational view of the preferred embodiment with a sample vial and tube shown in phantom;

FIG. 2 is an exploded view of the preferred embodiment with the vial and tube shown in phantom as above;

FIG. 3 is a plan view of the preferred embodiment;

FIG. 4 is an elevation view of the preferred embodiment;

FIG. 5 is a bottom view of the preferred embodiment;

BEST MODE FOR CARRYING OUT THE INVENTION

Figure 6:
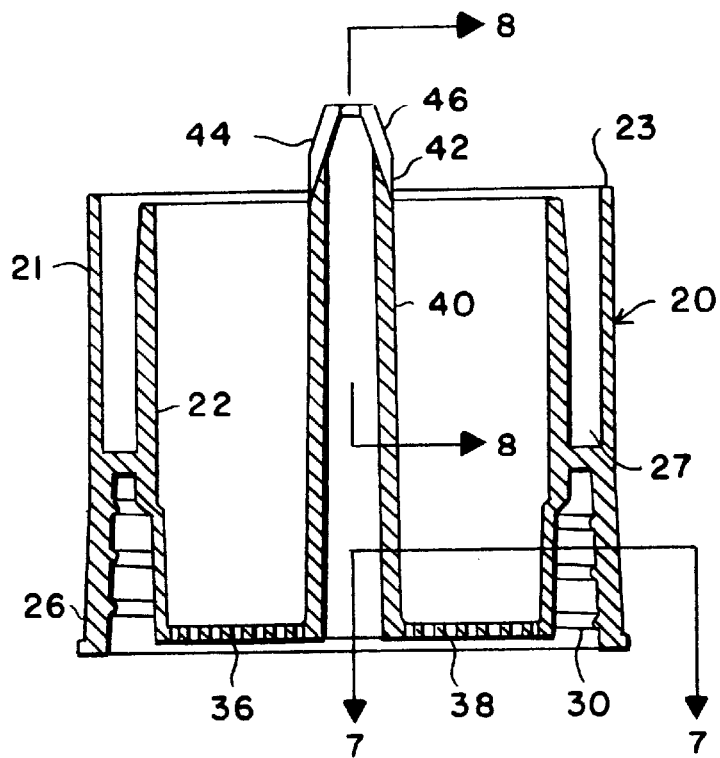
FIG. 6 is an enlarged cross sectional view of the preferred embodiment taken along the vertical centerline of the device.
Figure 7:
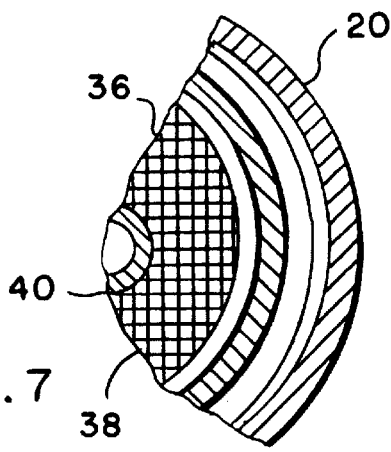
FIG. 7 is a cross sectional view taken along lines 7—7 of FIG. 6.

The best mode for carrying out the invention is presented in terms of a preferred embodiment.

The preferred embodiment as shown in FIGS. 1 through 9 is comprised of the following major elements; a cylindrical body 20, a sample vial 24, a centrifuge tube 28, an integral filter 36, a hollow stem 40 and orifices 46. The cylindrical body 20 is basically hollow and is made of a thermoplastic material such as polyethylene, polystyrene, in polycarbonate or the like with polypropylene preferred. The body 20 has sample vial connecting means integral with a first end 22 for fastening the conventional sample vial 24. Surrounding first end 22 is upstanding skirt portion 21 which is integral with body 20. The fastening is accomplished using an interference fit where the vial's threaded end is simply forced between skirt portion 21 and over the outside diameter of the body first end 22. This type of fit for vials of this type is well known in the art and produces a liquid tight seal. The preferred sample vial 24 utilized is the 30 milliliter size which is in common usage and readily available in the medical field.

Thus, it is apparent that any contaminant on the threaded or non-threaded end 25 of vial 24 is trapped or caught in the circumferential recess 27 formed between upstanding skirt portion 21 and first end portion 22. It is preferred that upstanding skirt portion 21 be molded integrally with body 20.

The body 20 further contains centrifuge tube connecting means integral with a second end 26 for fastening the conventional centrifuge tube 28. The fastening accomplished using male threads 30 that grip female threads, normally included in the centrifuge tube 28. The body 20 further contains an inwardly depending lip 32 that is located inward of the male threads 30 creating a sealing barrier between the tube 28 and the body 20 permitting a liquid tight seal to be made when the tube 28 is rotatably tightened into the body 20. The threaded portion of the body 20 fits over the tube 28 much like a cap.

The integral filter 36 extends into the centrifuge tube connecting means and is at right angles to the body 20, coaxially covering the entire cross sectional area of the cylindrical body. The filter 36 divides the internal space within the body between the vial 24 and tube 28 and is used to strain and retain access fecal debris such as undigested vegetable matter from the liquid diluent specimen that is contained within the sample vial 24. Thus, allowing only small particles in solution to pass into the tube 28 along with its is liquid diluent. The filter 36 is integrally formed with the body 20 and contains a multiplicity of perforated square openings 38 molded completely through. The openings 38 are from 0.5 millimeters to 0.7 millimeters in height and in width with 0.6 millimeters being preferred.

The hollow stem 40 is located in the center of the filter 36 and extends upward away from the filter surface, to about the height of upstanding skirt portion 21, so that a centrally upstanding hollow stem is provided. The stem 40 is parallel with the body first end 22 and functions to equalize the pressure between the vial 24 and the tube 28 when the liquid diluted fecal specimen is strained and flows therebetween.

The hollow stem 40 is best illustrated in the cross section of FIG. 6 and has an inwardly tapered shank 42 with an inside diameter of from 0.38 millimeter to 0.42 millimeters at the filter abutment end with 0.40 millimeters preferred. The upstanding end of the shank 42 has an inside diameter of from 0.30 millimeters to 0.34 millimeters with 0.32 millimeters being found to be ideal. The taper of the steam has a distinct bearing on its ability to equalize the pressure and has proven successful in the preferred relationship.

The hollow stem 40 terminates with a truncated end 44 that protrudes above the body first end 22 preferably 0.64 millimeters which is sufficient to properly equalize pressure relative to the liquid level, but is slightly below the circumferential edge 23 of upstanding skirt portion 21. The truncated end 44 further contains a number of geometrically shaped orifices 46 for air passage with the quantity of four orifices being favored.

Figure 8:
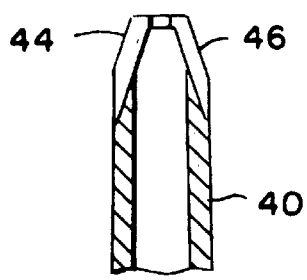
FIG. 8 is a cross sectional view taken along line 8—8 of FIG. 6 illustrating partially the cross section of the stem.
Figure 9:
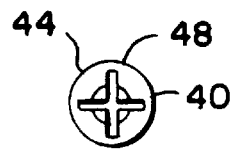
FIG. 9 is a view illustrating the top of the stem of the device shown in FIG. 6.

The preferred embodiment of orifice 46 is illustrated in FIGS. 3, 8 and 9 and consists of intersecting rectangular slots 48 forming a cross shape, two in each plane terminating at four places 90 degrees apart.

In function, the fecal parasite concentrator may use the commonly accepted Ritchie formula-ether method or Zierdt's method as described in the BACKGROUND ART discussion of U.S. Pat. No. 4,081,365. Any other modified or diverse methods may also be employed as long as they require the closed two tube system and filtration of a diluent with the sample in a liquid solution is required.

While the invention has been described in complete detail and pictorially shown in the accompanying drawings it is not to be limited to such details, since many changes and modifications may be made in the invention without departing form the spirit and scope thereof. Hence, it is described to cover any and all modifications and forms which may come within the language and scope of the appended claims.

What is claimed is:

1. A fecal parasite concentrator filter comprising:
   (a) a cylindrical body having a first upper end and a second lower end;
   (b) sample vial connection means integrally molded with the body first upper end and having an upwardly extending circumferential portion spaced from the body first upper end and forming a recess between said body first upper end and said sample vial connection means for fastening a sample vial containing a liquid diluent fecal specimen;

(c) centrifuge tube connection means integrally molded with the body second lower end for attaching a centrifuge tube thereupon;

(d) a filter integrally molded with the body and extending into the centrifuge tube connecting means and terminating across the body at right angles for straining and retaining excess fecal debris from a liquid diluent specimen;

(e) a hollow stem integrally molded with said filter, the hollow stem centrally upstanding and parallel with the body first upper end, the hollow stem abutting the filter at a filter abutment end being coterminous therewith, an upstanding end of the hollow stem at an opposite end to the filter abutment end, for equalizing pressure between the sample vial and the centrifuge tube connected to the body ends when liquid diluted fecal specimen flows therebetween; and (f) a truncated end inherent with the hollow stem having a plurality of orifices permitting air to pass therethrough while restricting solid matter.

2. The concentrator filter as recited in claim 1 wherein said body further comprises a thermoplastic material.

3. The concentrator filter as recited in claim 2 wherein said thermoplastic material further comprises polypropylene.

4. The concentrator filter as recited in claim 1 wherein said sample vial connection means further comprises an interference fit for sealing the first upper end of the body to a sample vial in a liquid tight manner.

5. The concentrator filter as recited in claim 1 wherein said centrifuge tube connection means further comprises a plurality of male threads that grippingly interface with female threads on a centrifuge tube and said body having an inwardly depending lip directly inward of the male threads creating a sealing barrier between the body and a centrifuge tube for a liquid tight interface.

6. The concentrator filter as recited in claim 1 wherein said filter having a multiplicity of perforated square openings from 0.5 millimeters to 0.7 millimeters.

7. The concentrator filter as recited in claim 1 wherein said hollow stem further comprises an inwardly tapered shank having an inside diameter of from 0.38 millimeters to 0.42 millimeters at the filter abutment end and 0.30 millimeters to 0.34 millimeters at the upstanding end.

8. The concentrator filter as recited in claim 1 wherein said truncated end protrudes above the body first upper end but below said upstanding circumferential portion.

9. The concentrator filter as recited in claim 1 wherein said hollow stem truncated end orifices are interceding rectangular slots forming a cross shape.

10. A concentrator filter comprising:

(a) a cylindrical body having a first upper end and a second lower end;

(b) vial connection means integrally molded with the body first upper end and having an upstanding, circumferential portion spaced from the body first upper end and forming a recess between said body first upper end and said vial connection means for fastening a vial containing a liquid specimen;

(c) centrifuge tube connection means integrally molded with the body second lower end for attaching a centrifuge tube thereupon;

(d) a filter integrally molded with the body and extending into the centrifuge tube connecting means and terminating across the body at right angles for straining and retaining excess debris from a liquid diluent specimen;

(e) a hollow stem integrally molded with said filter, the hollow stem being upstanding and parallel with the body first upper end, the hollow stem abutting the filter at a filter abutment end and being coterminous therewith, for equalizing pressure between the vial and the centrifuge tube connected to the body ends when a liquid diluted specimen flows therebetween; and (f) an end inherent with the hollow stem and having at least one orifice permitting air to pass therethrough while restricting solid matter.

\* \* \* \* \*